(12) United States Patent
Yu et al.

(10) Patent No.: US 9,974,449 B2
(45) Date of Patent: May 22, 2018

(54) METHOD AND APPARATUS FOR ARTERIAL BLOOD PRESSURE MEASUREMENT AND INDIVIDUALIZED RECTIFYING TECHNOLOGY

(76) Inventors: Meng-Sun Yu, Beijing (CN); Hai-Yan Xiang, Beijing (CN); Zu-Lai Tao, Beijing (CN)

(*) Notice: Subject to any disclaimer, the term of this patent is extended or adjusted under 35 U.S.C. 154(b) by 897 days.

(21) Appl. No.: 13/466,086

(22) Filed: May 7, 2012

(65) Prior Publication Data

US 2012/0283584 A1 Nov. 8, 2012

Related U.S. Application Data

(63) Continuation-in-part of application No. 11/775,870, filed on Jul. 11, 2007, now abandoned.

(51) Int. Cl.
| | |
|---|---|
| *A61B 5/02* | (2006.01) |
| *A61B 5/0225* | (2006.01) |
| *A61B 5/022* | (2006.01) |
| *G06Q 30/02* | (2012.01) |

(52) U.S. Cl.
CPC ........ *A61B 5/0225* (2013.01); *A61B 5/02208* (2013.01); *G06Q 30/0202* (2013.01)

(58) Field of Classification Search
CPC .............. A61B 5/02208; A61B 5/0225; A61B 5/02225
USPC .................................................. 600/490–499
See application file for complete search history.

(56) References Cited

U.S. PATENT DOCUMENTS

| | | | | | |
|---|---|---|---|---|---|
| 4,216,779 A | * | 8/1980 | Squires | .............. | A61B 5/02208 128/900 |
| 4,408,614 A | * | 10/1983 | Weaver | .............. | A61B 5/02208 428/682 |
| 4,974,597 A | * | 12/1990 | Walloch | .............. | A61B 5/02208 600/493 |

(Continued)

*Primary Examiner* — Tiffany Weston
(74) *Attorney, Agent, or Firm* — Kile Park Reed & Houtteman PLLC

(57) ABSTRACT

A method and apparatus for indirect, quantitative estimation of beat-to-beat arterial blood pressure utilizing the individualized rectifying technique. A function $T_K=H(P)$ that describes the relationship between Korotkoff's sound delay time $T_k$ and cuff pressure P is obtained by measuring the different cuff pressure P and corresponding $T_k$ in the Korotkoff's sound sensor that is distal to the cuff. Keep the cuff pressure at a constant value $P_m$, the blood pressure variance can be calculated using the Korotkoff's sound delay time $T_{km}$, according to the function $T_k=H(P)$. The invention can measure the beat-to-beat artery blood pressure indirectly. The technique can be applied to obtain individual coefficient of regress equation for continuous arterial blood pressure measurement by the instantaneous blood pressure fluctuation, which make the rectifying technique more safe, effective and less erroneous. The technique makes the operation of noninvasive continuous blood pressure measurement for long time more practical.

2 Claims, 8 Drawing Sheets

(56) References Cited

U.S. PATENT DOCUMENTS

| | | | | |
|---|---|---|---|---|
| 5,322,069 A | * | 6/1994 | Gallant | A61B 5/0205 |
| | | | | 128/900 |
| 5,560,365 A | * | 10/1996 | Ogura | A61B 5/02208 |
| | | | | 600/493 |
| 5,634,467 A | * | 6/1997 | Nevo | A61B 5/0225 |
| | | | | 600/485 |
| 2003/0220577 A1 | * | 11/2003 | Bartels | A61B 5/02125 |
| | | | | 600/510 |
| 2005/0261597 A1 | * | 11/2005 | Kolluri et al. | 600/513 |
| 2008/0033310 A1 | * | 2/2008 | Yu et al. | 600/493 |

* cited by examiner

METHOD AND APPARATUS FOR ARTERIAL BLOOD PRESSURE MEASUREMENT AND INDIVIDUALIZED RECTIFYING TECHNOLOGY

TECHNOLOGY

This is a continuation-in-part application of patent application Ser. No. 11/775,870 filed on Jul. 11, 2007, now abandoned which is pending now, and the entirety of which is incorporated by reference herein and made a part of this specification.

FIELD OF THE INVENTION

The present invention relates in both a method and apparatus for noninvasive arterial blood pressure measurement and individualized rectifying technology for beat-to-beat blood pressure measurement.

BACKGROUND OF THE INVENTION

Noninvasive blood pressure (BP) measurement is the technology that measures the BP indirectly by the arterial vessel wall beat or arterial volume. There are two types of noninvasive BP measurement technology: intermissive measurement and continuous measurement. Intermissive measurement can get the value of BP at different time points. But due to the consistent change of BP between every two heart beats and every two time points, the systolic pressure and diastolic may not represent the meaningful value, of course, this two values relate to different heart beats. Continuous measurement technology, which measures the BP without intermission, can provide the beat-to-beat BP or continuous BP oscillation. It is very important to realize the noninvasive continuous BP measurement. But, until now, there is not an accurate method that can achieve the aim.

BP measurement in according to the pulse wave transit velocity (PWTV) is a type of noninvasive continuous BP measurement method. In 1922, Bazzett discovered that arterial pressure related to the PWTV or pulse wave transit time (PWTT), in addition to arterial volume and arterial flexibility. In 1957, Lansdown pointed that PWTT and arterial BP present linear relationship to some extent and this relationship is stable for a given subject in a period of time. Moreover, the coefficients that descript linear relationship between PWTT and BP vary violently for different subjects with different arterial vessel tissue structure. But in past studies, the BP of different subject was general evaluated through the same coefficient, so the result can be distorted by errors.

An equation describing the relationship between the BP and PWTT for a given subject can be deduced in terms of the linear relationship between them:

$$BP = a + b \times PWTT \quad (A)$$

In this formula, b is regressing coefficient to be estimated which varies in different subjects. But for a given subject and in a short period, a and b are stable. Previous analyze shows that to evaluate arterial BP, the coefficient a and b for a given individual must be obtained firstly. After that, BP can be computed By the PWTT (or PWTV). The coefficient a and b need to be rectified by means of individualized regressing technology, so the BP computed by the regressing equation (A) can fit individual condition well.

In principle, evaluating two parameters needs two group independent experiment data. PWTT and mean arterial pressure in the quiet condition can be obtained, so coefficient a, i.e. intercept, is easy to get. To $b = \Delta BP / \Delta PWTT$, i.e. slope, is always estimated by altering BP to get two groups of data. But, in order to change BP, exercise or drugs were often involved in the experiment, which can change the artery character and violate the premise that in a short period linear relationship in equation (A) is consistent.

Yu Mengsun also believed that when body posture changed (for example, supine and elevating leg), PWTT in the elevating leg would change. It is because that the change of body posture alters the pressure in some vessel and then makes PWTV different from that of normal state. If experiment data in normal status and posture changing status can be obtained, the coefficient b will be estimated from these data. This method can rectify parameters more accurately, but multi-group information in relate to the beat-to-beat BP cannot be got continuously when the body posture changed.

SUMMARY OF THE INVENTION

The purpose of the present invention is to offer a method and device that can measure the beat-to-beat arterial blood pressure by the information of arterial blood pressure. The invention also propose an individual rectifying technique which makes the blood pressure estimated by using continuous pulse wave measurement to be according with the individual reality.

To resolve the problem above, the invention uses a method to measure the arterial blood pressure:

(1) Wrapping the cuff around the trunk or limb of the subject; getting a series value of cuff pressure P and corresponding Korotkoff's sound delay time $T_K$; getting function relation $T_K = H(P)$ between Korotkoff's sound delay time and of cuff pressure.

(2) Calculating Korotkoff's sound delay time under the corresponding cuff pressure (Pm); according to the fact that the change of delay time caused by change of cuff pressure is approximately equal in magnitude and inverse in phase compared with the change caused by blood pressure, using the equation relation $T_K = H(P)$ between Korotkoff's sound delay time $T_K$ and cuff pressure P. We can estimate the change of blood pressure, which is corresponding to the Korotkoff's sound delay time.

The Korotkoff's sound delay time mentioned above is the time that the Korotkoff's sound arrived the fixed reference point within the same cycle of a heartbeat. The fixed reference point can be the ECG R wave peak (FIG. 1) or the ascending edge of pulse wave in cuff (FIG. 2).

The equipment to implement the method above comprises: the cuff, the inflating unit and deflating unit for the cuff, the cuff pressure sensor, the Korotkoff's sound sensor, ECG electrode. The ports of output signal of the cuff pressure sensor and Korotkoff's sound sensor connected with the microprocessor through the signal conditioning circuit. The ECG electrode connected with the microprocessor, which has the printing and data display equipment.

The individual rectifying technique according to the said invention is:

Constructed a regress equation between pulse wave transit time (PWTT) and beat-to-beat arterial blood pressure (BP), $$BP = a + b \times PWTT \quad (A)$$

In the equation, BP is the arterial blood pressure, PWTT is the pulse wave transit time corresponding to the BP, and the parameters b is the regress coefficient. After individualized rectified the parameters a and b, based on the continuous measurement of pulse wave transit time, using the equation above, we estimated the continuous change of the individual blood pressure. The individual rectifying method for b is:

(1) Wrapping the cuff around the trunk or limb of the given subject, getting a series value of cuff pressure P and corresponding Korotkoff's sound delay time $T_K$, then we can get the function relation $T_K$=H(P) between Korotkoff's sound delay time and cuff pressure.

(2) Calculating Korotkoff's sound delay time under the corresponding cuff pressure $P_m$, using the function relation $T_K$=H(P) between Korotkoff's sound delay time and variety of cuff pressure, we can estimate the change value of blood pressure corresponding with the Korotkoff's sound delay time.

(3) Recording the pulse wave transit times corresponding to the Korotkoff's sound delay time in step 2.

(4) According to the data measured in step 2 and 3, calculating the regress coefficient between the change of mean arterial pressure ΔBP and the change of pulse wave transit time ΔPWTT, then we can obtain individual rectified parameter b.

In step 2 of the individual rectifying method, the mean arterial pressure Pm is the preference for the cuff pressure.

Another method of individual rectifying is: during the measurement of the Korotkoff's sound delay time when cuff pressure in the step 2, by acting the behavior that can alter the blood pressure of the subject and do not change the characteristic of vascular wall, we can enhance the change of blood pressure between different measurement points.

The behavior that can alter the blood pressure of the subject is deep breathing.

The equation above-mentioned that was constructed for the subject is a regress equation between the PWTT and BP. The method in present invention is the same with the equation between PWTV (pulse wave transit velocity) and BP, or other linear regress equations that have different performs but the same essence.

The present invention is designed according to the study about the relationship of Korotkoff's sound delay time $T_K$, the cuff pressure P and arterial blood pressure BP. The following is the introduction of the invention principle.

When measuring blood pressure by the conventional stethoscope method, we firstly inflate the cuff until the cuff pressure exceeding to systolic blood pressure when artery is impacted and shuts off, there is no blood flow in the artery. Then deflate the cuff slowly; referring to FIG. 1, when the cuff pressure is somewhat under the systolic blood pressure, the first Korotkoff's sound that is corresponding to the time when artery began to open appears. We discover the following orderliness: in a series of the times when artery open, the interval $T_1$ from the first Korotkoff's sound to R wave in the electrocardiogram is the longest, while the intervals $T_2$, $T_3$ . . . from the subsequent Korotkoff's sounds to R wave in the electrocardiogram are shorter and shorter respectively, and the shortest one appears at the time of the last Korotkoff's sound. Referring to FIG. 2, if the rising point of the pulse wave inside the cuff is used for the reference point, then Korotkoff's sound delay time $T_K$ can also be defined as the time interval from the rising point of the pulse wave inside the cuff to the appearance of the Korotkoff's sound. Similarly, along with the cuff pressure P decreasing, Korotkoff's sound delay times $T_1$, $T_2$, $T_3$ . . . with each heartbeat cycle become shorter and shorter.

To analyze the principle of the phenomenon, we find that the pressure change inside the artery is a gradual process other than upright rising. So along with the decreasing of the pressure inside cuff, within each heartbeat cycle, the earlier artery open, the earlier Korotkoff's sound appears. And also according to the fixed reference point in each corresponding cycle (such as R wave in electrocardiogram or the rising point of the pulse wave inside the cuff or some other selected reference point), Korotkoff's sound delay times are shorter and shorter.

We can draw a conclusion that Korotkoff's sound delay times decrease gradually along with the dropping of the cuff pressure, so the function relationship which is formed from a series of Korotkoff's sound delay times $T_K$ and their corresponding cuff pressure P (referring to FIG. 3) in a whole deflating process can be drawn as a line approximation (referring to FIG. 4, L1 is a simple line approximation, L2 is a quadratic line approximation).

Additionally, FIG. 5 shows the line approximation of the $T_K$=H(P) corresponding to different blood pressure level. In the figure, the line approximation corresponding to the higher blood pressure L2 sits left to the line approximation corresponding to lower blood pressure L1. So we can know that, at the same level of cuff pressure, the Korotkoff's sound delay time corresponding to the higher blood pressure is lower than the Korotkoff's sound delay time corresponding to the lower blood pressure, and at different level of cuff pressure, the changes of Korotkoff's sound delay time corresponding to unit cuff pressure change $dT_K/dP$ are different as well.

The above-mentioned function relationship $T_K$=H(P) is obtained when cuff pressure is descending, at the same time, we observe that if cuff pressure is at a constant pressure between systolic blood pressure and diastolic blood pressure, pressure change inside the artery will result in the change of artery transmural pressure, consequently, Korotkoff's sound delay time will change. It can be considered that the change of Korotkoff's sound delay time induced by cuff pressure change when blood pressure is stable is the same in size and inversely in direction of that induced by blood pressure change when cuff pressure is stable.

According to the above-mentioned orderliness, the present invention estimates the blood pressure change of each heartbeat cycle corresponding to each Korotkoff's sound by observing Korotkoff's sound delay time under certain cuff pressure. The method can also evaluate the blood pressure of each cycle.

The individualized rectifying technology of continuous artery blood pressure monitoring regress equation is established on the finding that the corresponding change of artery blood pressure can be estimated by the Korotkoff's sound delay time. The following is the principle of this technology:

Supposing the regress equation between pulse wave transit time PWTT and beat-to-beat artery blood pressure BP is:

$$BP = a + b \times PWTT \tag{A}$$

Before using PWTT to measure BP, the parameters a and b must be calculated. With some technologies, the subject's mean arterial blood pressure $BP_0$ and corresponding pulse wave transit time $PWTT_0$ can be measured. So the parameter a will be easy to get if the parameter b has been gotten. With two groups of blood pressure values and PWTT values at different blood pressure level, the parameter b can be obtained. There are two factors:

1. To change the value of the BP;
2. To detect the change of the BP.

In fact, the human's BP is changing at any moment. But the instantaneous change of BP can't be measured non-invasively with the known technique. The present invention can estimate the change of BP per beat through the Korotkoff's sound delay time, and measure individual rectifying parameters using instantaneous change of BP.

Otherwise, the change of BP and PWTT are so small that the error of calculation will increase inescapably. In order to increase the Signal-to-Noise Ratio (SNR) and get the bigger instantaneous change of BP, the prior project of this invention also try to control breath or some other actions to alter the subject's BP.

The work process of the present invention is: the cuff pressure P can be increased or decreased by inflation unit. In this process, Korotkoff's sound sensor measures the arrived time of sound, and sends it to the CPU. At the same time, heart beat signal is also sent to the CPU through electrodes and detecting circuit. Thereby the value of interval $T_K$ that is from every fixed reference point to Korotkoff's start-point in the same cycle can be gotten. And the function $T_K=H(P)$ in said invention can be obtained. Keeping the cuff pressure at a fixed value, measuring Korotkoff's sound delay time $T_{Km}$, using function $T_K=H(P)$ to get the blood pressure variance in the current heart cycle compared to the initial measurement when the function $T_K=H(P)$ was obtained.

The method and equipment in present invention can fulfill beat-to-beat artery blood pressure estimation, and create a new way for individualized rectifying technology of continuous artery blood pressure monitoring regress equation. This technology can use instantaneous change of BP to get individual rectifying parameters, and increase the possibility of technical realization for long-time noninvasive continuous blood pressure monitoring, with many merits such as safety, availability, less error and briefness.

The present invention apply deep breath to enhance the blood pressure variety of subject in individualized rectifying method, which can improve the accuracy of rectifying and reduce the errors and is safe and reliable for the subject.

DETAILED DESCRIPTION OF THE EMBODIMENTS

Embodiment 1

Figure 13:
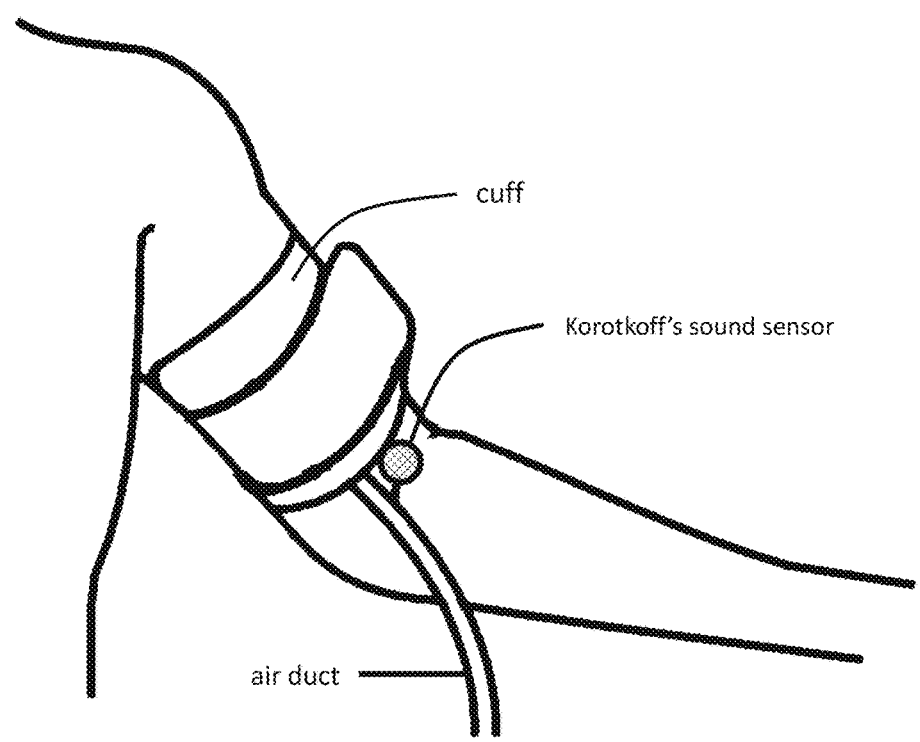
FIG. 13 illustrates a cuff wrapped around an arm of a given subject.

The following is about how to measure the arterial BP value of certain heartbeat:

1. Wrapping the cuff around a subject's upper arm as shown in FIG. 13, obtaining mean blood pressure value $BP_0$ by oscillometric or auscultatory method, and measuring pulse wave transit time value $PWTT_0$ simultaneously.

2. Recording a series of Korotkoff's sound delay time value $T_K$ and cuff pressure value P during deflation, then construct function $T_K=H(P)$ between the Korotkoff's sound delay time and the cuff pressure value when the subject's mean blood pressure is at the level of $BP_0$. Obtaining the curve that the Korotkoff's sound delay time is shortening as the cuff pressure decreases after quadratic line approximation about these discrete data. And according to $T_K=H(P)$, the function g(P) about the $dT_K/dP$ value of each point is obtained too. As show in FIG. 9 ($g(P)=dT_K/dP$).

Based on these individualized functions said, the following data can be measured and calculated.

3. Measuring Korotkoff's sound delay time value $T_{Km}$ when the cuff pressure is at certain known value Pm that is between systolic blood pressure SBP and diastolic blood pressure DBP. Based on the said function $T_K=H(P)$, obtaining Korotkoff's sound delay time $T_{Km0}$ when the cuff pressure value is equal to $P_m$, and calculate the difference $\Delta T_{Km}$ between $T_{Km}$ and $T_{Km0}$.

4. Calculating the $g(P_m)$ value as the cuff pressure value is equal to $P_m$, according to the said function g(P), in which the $dT_K/dP$ of each point changes with the cuff pressure value P.

5. Based on the equation: $g(P_m)=\Delta T_{Km}/\Delta BP_m$, obtaining the BP changes value $\Delta BP_m$ corresponding to the Korotkoff's sound delay time value $T_{Km}$.

The blood pressure value of this beat is equal to the summation of BP variance $\Delta BP_m$ and the mean blood pressure value $BP_0$ that is used to get the function $T_K=H(P)$.

Figure 5:
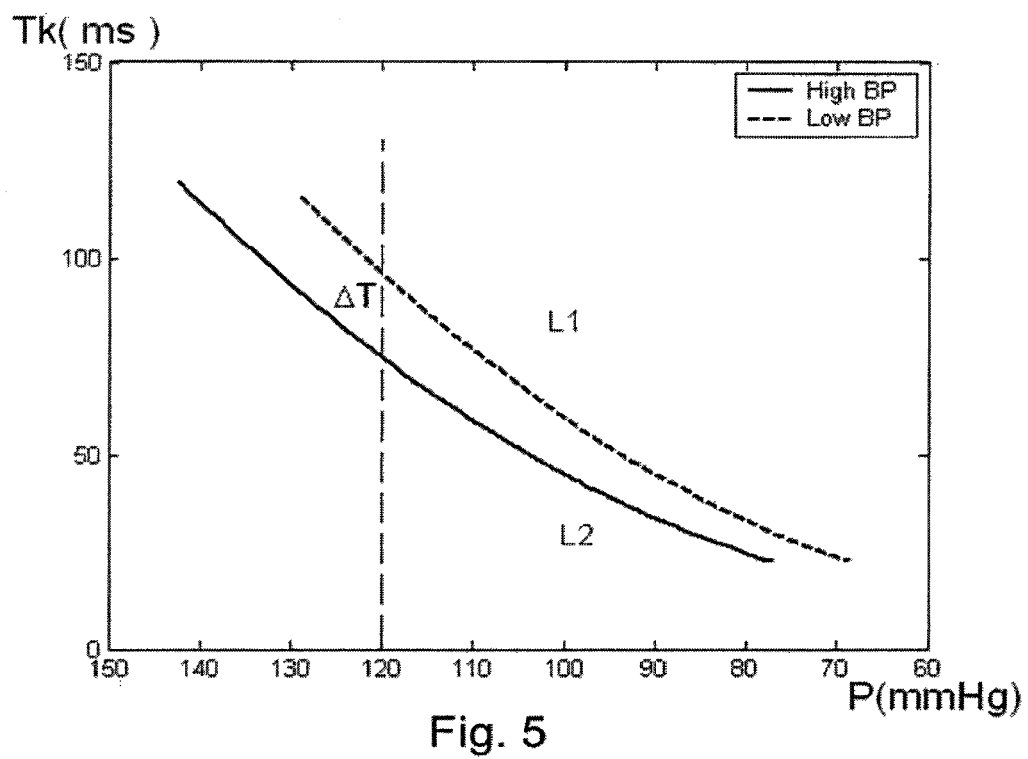
FIG. 5 is the line approximation of the Korotkoff's sound delay time $T_K$ and cuff pressure P at different blood pressure level.
Figure 6:
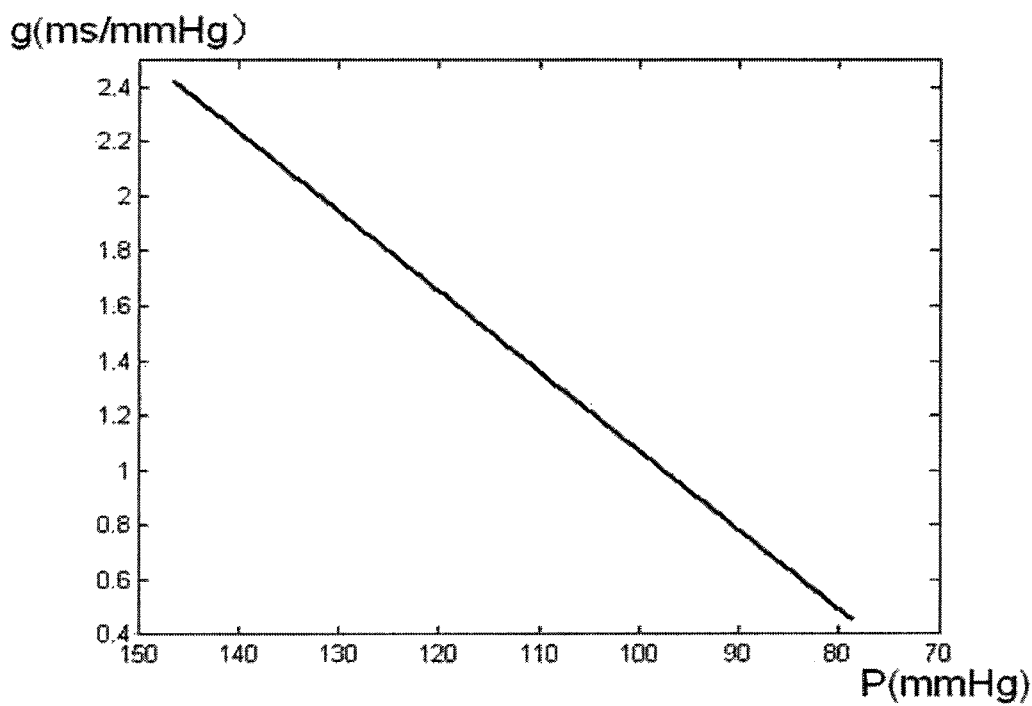
FIG. 6 is the relationship between $dT_K/dP$ and cuff pressure P.

The principle of the said method is follows: If the BP level at the time when the $T_{Km}$ is measured is equal to the BP level $BP_0$ at the time when the function $T_K=H(P)$ was established, the obtained Korotkoff's sound delay time value $T_{Km}$ should be equal to Korotkoff's sound delay time value $T_{Km0}$ which is calculate from the fitted curve $T_K=H(P)$ while the pressure is equal to $P_m$. Otherwise, it means that the BP has changed. If the blood pressure increases, the delay time value $T_{Km}$ is shorter; and if the blood pressure decreases, the delay time value $T_{Km}$ is longer (shown as FIG. 5). According to the phenomena that the change of Korotkoff's sound delay time induced by cuff pressure change when blood pressure keep stable is the same in size and inversely in direction of that induced by blood pressure change when cuff pressure is stable, the BP change value related to the delay time $T_{Km}$ can be calculated.

Embodiment 2

Figure 7:
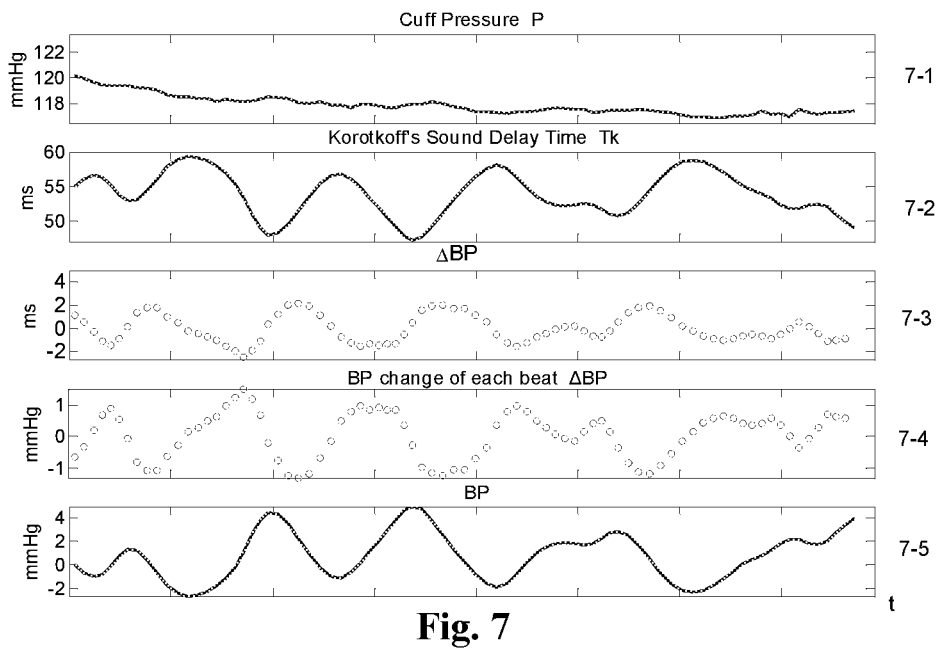
FIG. 7 is the process of the data acquiring and transact in embodiment 2.

This is about how to measure beat-to-beat arterial blood pressure. FIG. 7 shows the course of data acquiring and signal processing. Following is the detail:

1. obtaining a series of Korotkoff's sound delay time value $T_K$ and corresponding cuff pressure value P, and construct function $T_K=H(P)$ as in embodiment 1. After two order fitting about these discrete data, establishing the curve $T_K=H(P)$ that Korotkoff's sound delay time value $T_K$ changed with cuff pressure value P.

Figure 9:
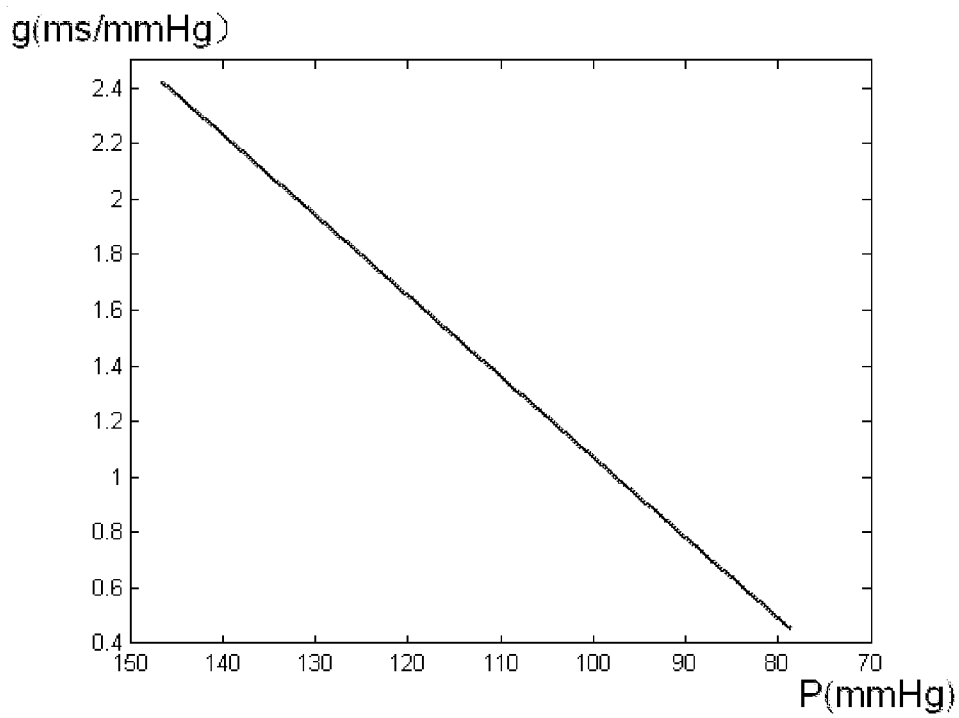
FIG. 9 is the relationship between $dT_K/dP$ and cuff pressure P according to the line approximation $T_K=H(P)$ in FIG. 8.

2. Calculating the difference value of the fitted curve $T_K$=H (P) in said, and obtains a new function g(P) that represents the Korotkoff's sound delay time change with one unit pressure (1 mmHg). As shown in FIG. 9.

3. Maintaining the cuff pressure at the level $P_0$ that is approximate equal to mean blood pressure, and then getting a series of beat-to-beat Korotkoff's sound delay time T(i) (shown as FIG. 7-2).

4. Calculating the difference T'(i) of the said T(i) (shown as 7-3). The relationship is shown as the following equation.

$$T'(i)=T(i+1)-T(i) \ldots (i=1, 2, 3 \ldots)$$

Figure 4:
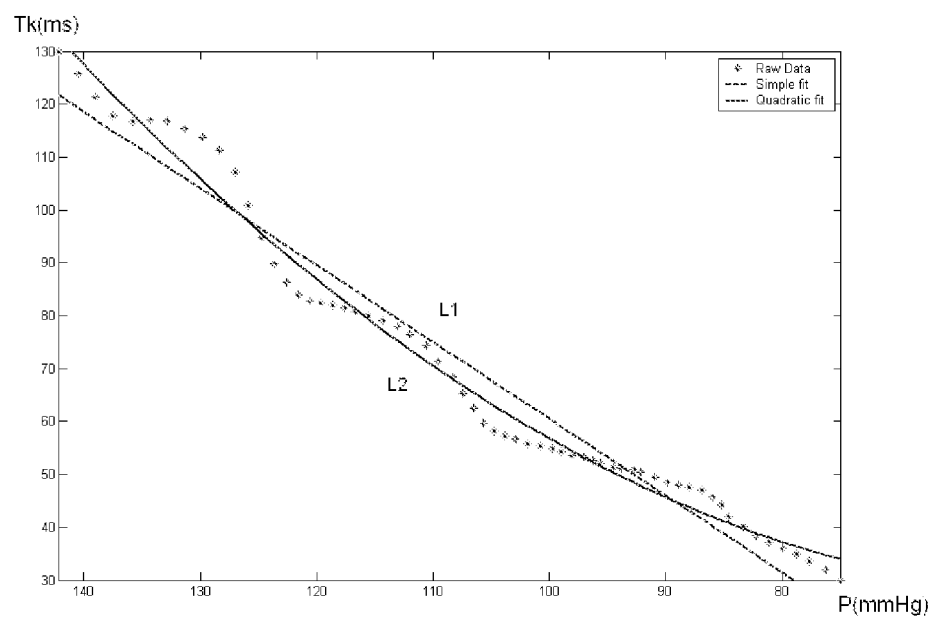
FIG. 4 is the simple line approximation and quadratic line approximation of the Korotkoff's sound delay time $T_K$ and cuff pressure P.

5. Each T'(i) is corresponding to a known cuff pressure $P_i$, and each pressure $P_i$ is corresponding to a unique data $g(P_i)=dT_K/dP$. Therefore, calculate the dynamic BP change value ΔBP(i) of each beat by the coefficient $g(P_i)$ corresponding to the T'(i) (shown as FIG. 7-4).

$$\Delta BP(i)=T'(i)/g(P_i)$$

Add up ΔBP(i) of each beat, and obtain the beat-to-beat continuous BP change value BP(n) (show as FIG. 7-5):

$$BP(n) = \sum_{i=1}^{n} \Delta BP(i)$$

n=1 . . . m−1,n is the heartbeat number during the cuff pressure keeps approximate stable, BP is the dynamic blood pressure. According to the equation above, the beat-to beat BP change can be calculated.

The calculated arterial blood pressure change is more close to the actual status when the cuff pressure is at the level of mean blood pressure value or close to it.

Embodiment 3

This is an embodiment to implement individually rectifying of said arterial blood pressure measurement.

The regress equation of PWTT and beat-to-beat arterial blood pressure BP is:

$$BP=a+b\times PWTT \qquad (A)$$

BP means blood pressure, PWTT means pulse wave transmit time, b means regress coefficient to be defined.

The method of individually rectifying of coefficient a and b is as follows:

(1) Putting the cuff and Korotkoff's sound sensor to the distal of the cuff on one of the upper arms of the subject, measuring the blood pressure by auscultatory method, get the systolic blood pressure and diastolic blood pressure, calculate the mean artery pressure $BP_0$ by empirical formula, (which can also be measured by oscillometrc method) and record the synchronous pulse wave transmit time ($PWTT_0$).

(2) Getting a series of pulse wave transmit times and cuff pressures in the whole deflating process in the same way as (1), building the function $T_K(P)$; getting the curve of Korotkoff's sound delay time $T_K$ changing with cuff pressure P, $T_K$ (P), calculating the difference of the curve, get the Korotkoff's sound delay times changing with each per unit pressure (1 mmHg), forming a new series function g(P). As shown in FIG. 9.

(3) Keeping the cuff pressure at a constant pressure between systolic blood pressure and diastolic blood pressure, getting a series of beat-to-beat Korotkoff's sound delay time and corresponding pulse wave transmit times. In measurement process, make the subject have deep breath, getting two group data arbitrarily, calculate the difference of Korotkoff's sound delay times in different time, ΔT. Based on the series function g(P), calculating the value g of corresponding cuff pressure, using ΔT to estimate the variation of arterial blood pressure $\Delta BP_1$; calculating the synchronous pulse wave transmit time $\Delta PWTT_1$.

The regressive coefficient $b_1=\Delta BP_1/\Delta PWTT_1$.

In the same way, get the $b_2$, $b_3$ . . . .

Calculate the mean of the series $b_1$, $b_2$, $b_3$ . . . , thus the regressive coefficient can represent the true individual parameters.

Figure 10:
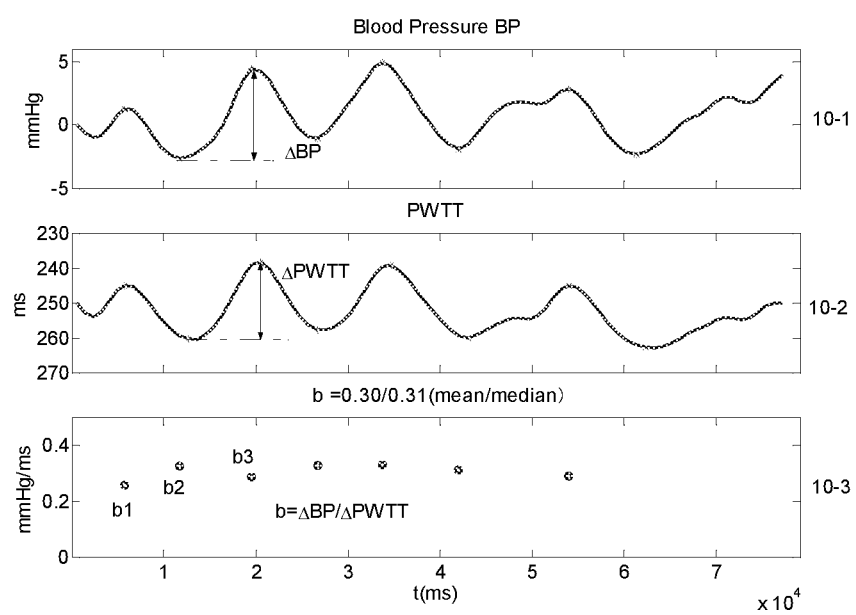
FIG. 10 is the process of calculating regress coefficient b in embodiment 3.
Figure 11:
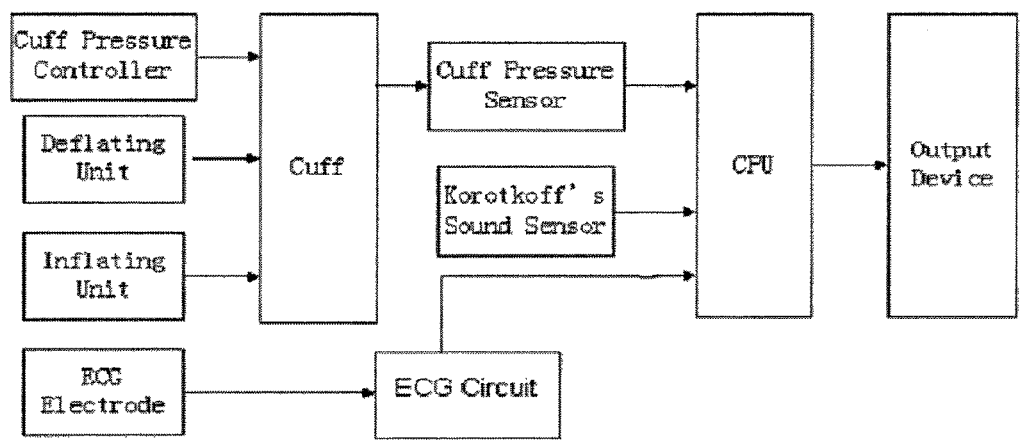
FIG. 11 is the diagram of the device of arterial blood pressure measurement.

FIG. 10, from top to bottom, represents the vary blood pressure changing with the Korotkoff's sound delay time, pulse wave transmit time PWTT, and the coefficient b of the blood pressure function, which calculated by the ratio of peak and trough. Calculate the mean or of the series $b_1$, $b_2$, $b_3$ . . . , which is the final coefficient b.

In addition, calculating the regressive coefficient using the BP signal and the PWTT signal, and the regressive coefficient is the coefficient b of the blood pressure function.

Figure 12:
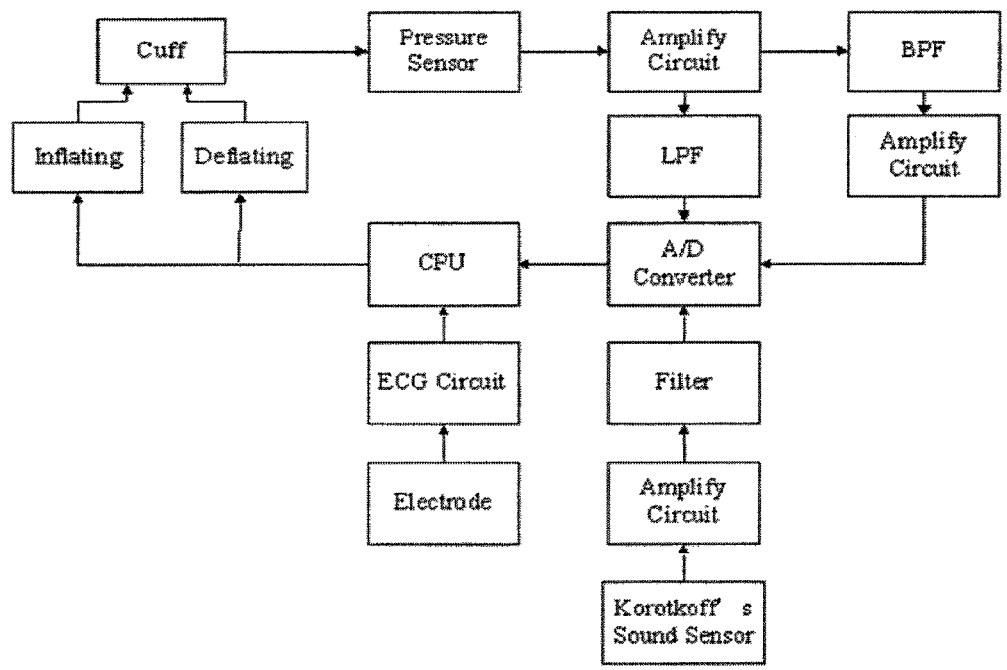
FIG. 12 is the diagram of the embodiment of artery blood pressure measurement device.

FIG. 12 is the diagram of the arterial blood pressure measurement apparatus.

In this embodiment, the controlling unit of inflating and deflating connects to CPU. The CPU controls the inflating and deflating, the analog signal output from the cuff pressure sensor were amplified, low-pass and band-pass filtered, and converted to digital signals and input to CPU; the output signal of Korotkoff's sound sensor was amplified, filtered, converted to digital signal and input to CPU, electrocardiogram circuits connect electrode and CPU.

Figure 1:
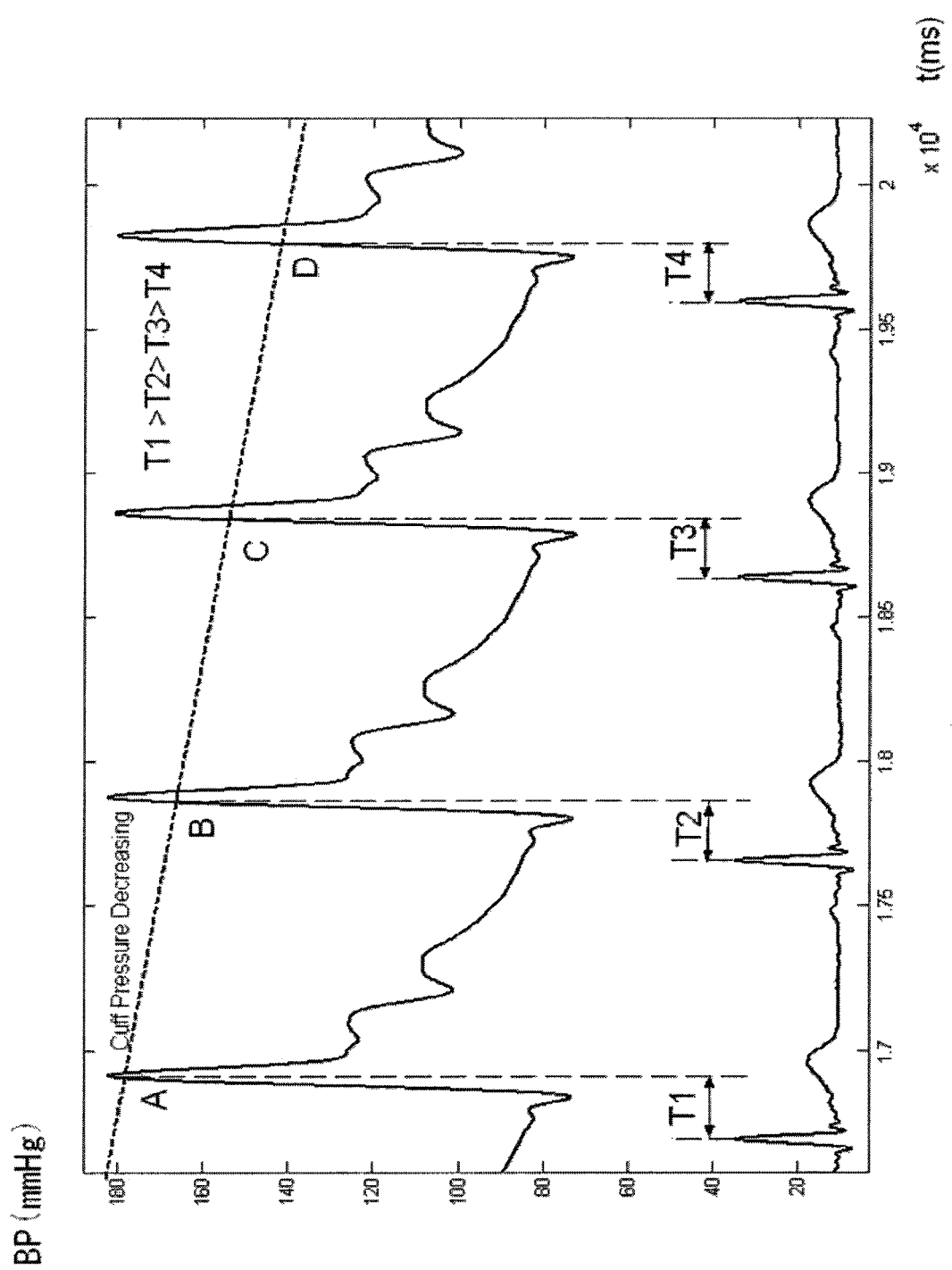
FIG. 1 is the Korotkoff's sound delay time $T_K$ with ECG R wave as reference point when cuff pressure decreasing.
Figure 2:
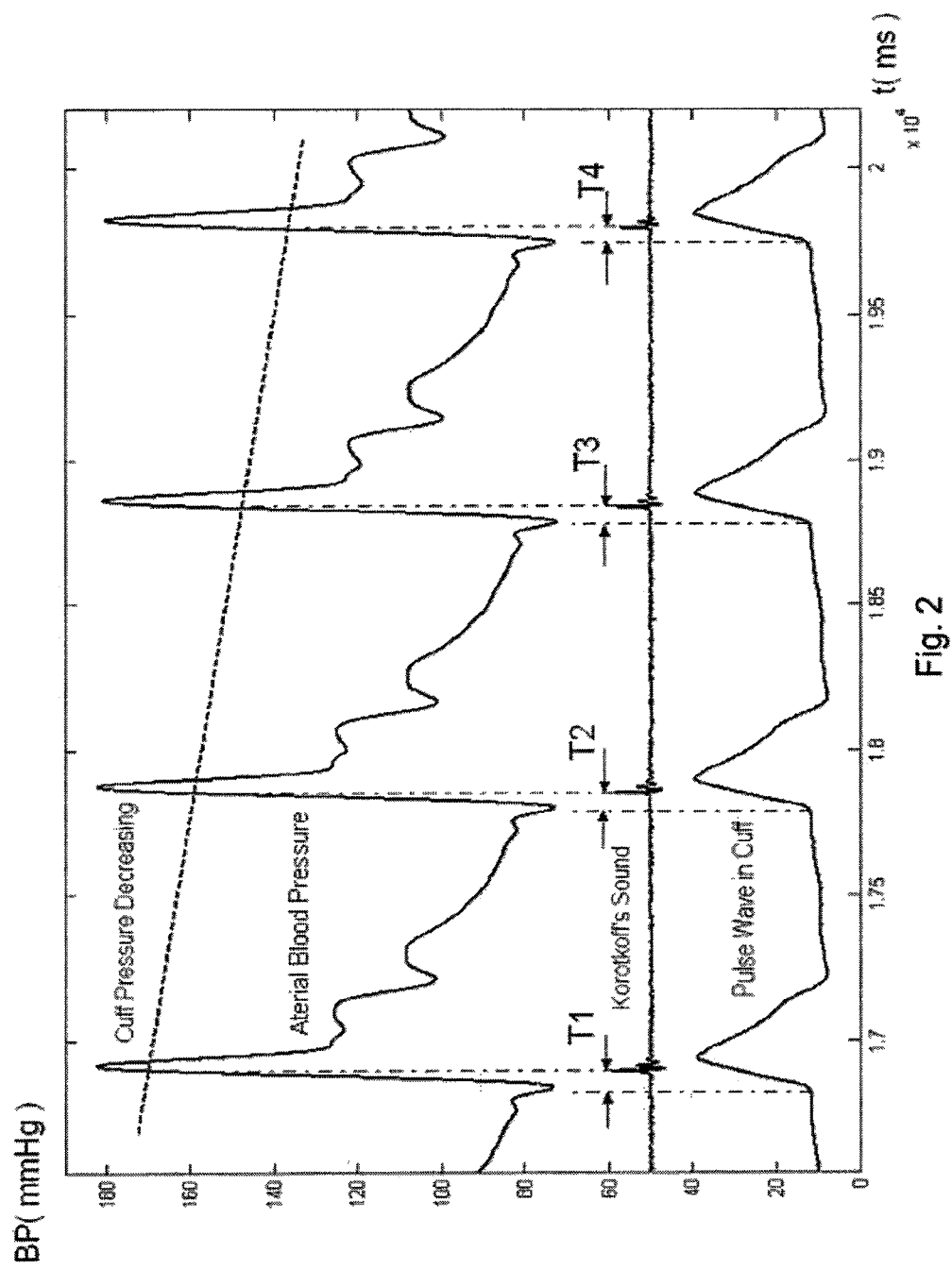
FIG. 2 is the Korotkoff's sound delay time $T_K$ with cuff pulse wave's raising point as reference point when cuff pressure decreasing.
Figure 3:
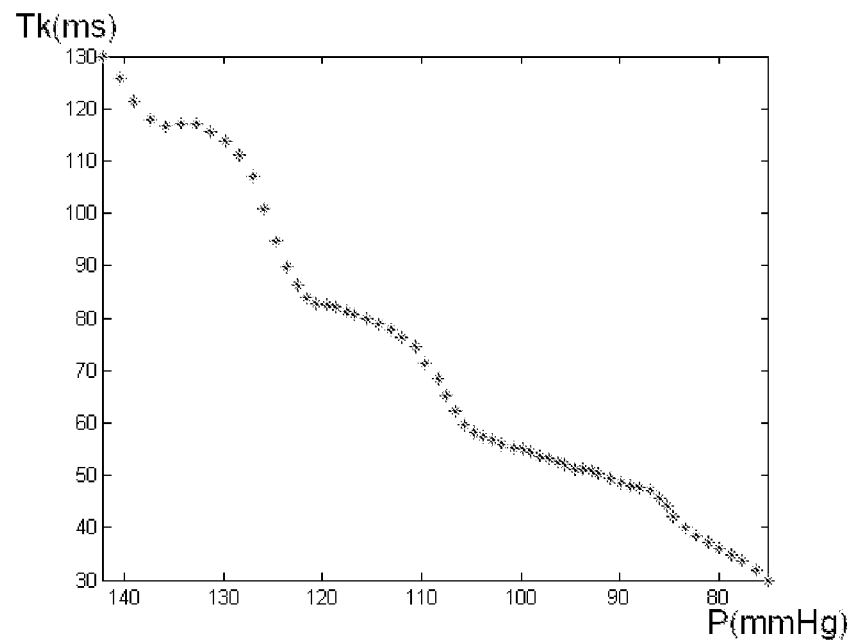
FIG. 3 is the relationship between Korotkoff's sound delay time $T_K$ and cuff pressure P.
Figure 8:
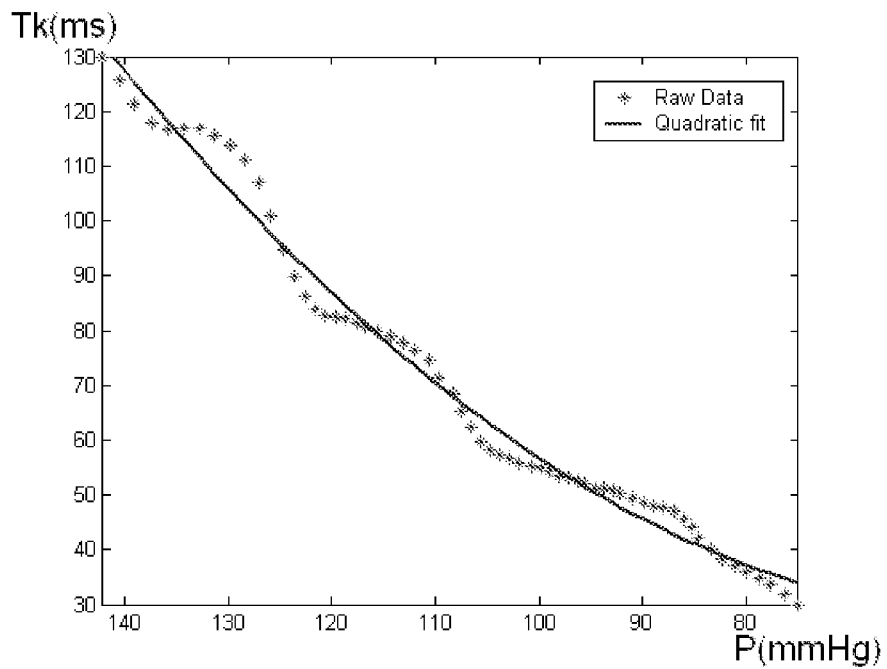
FIG. 8 is the relationship between $T_K$ and P and the quadratic line approximation of $T_K=H(P)$ in embodiment 1.

The CPU identifies the characteristic points of the Korotkoff's sound signal and the pulse wave signal in the cuff (As shown in FIG. 2). Then the CPU calculates the interval $T_k$ between the two groups of characteristic points. According to the $T_k$ values and the corresponding cuff pressure, the CPU perform curve fitting (FIG. 8) and the differences of the fitted $T_k$ are also calculated by the CPU (FIG. 9). The CPU calculates the estimated change in blood pressure for each heartbeat and accumulates the change of each beat to obtain the beat-to-beat blood pressure (FIG. 7). The CPU also calculates the coefficient b in blood pressure equation (A) according to the obtained BP and the PWTT (FIG. 10).

What is claimed is:

1. A method for noninvasive continuous measuring arterial blood pressure by using instruments including a blood pressure cuff, an inflating unit and a deflating unit for the blood pressure cuff, a cuff pressure sensor, a Korotkoff's sound sensor, an ECG electrode, a microprocessor, a signal processing circuit connected between the cuff pressure sensor, the Korotkoff's sound sensor and the microprocessor, and an ECG circuit connected between the ECG electrode and the microprocessor, comprising the steps of:

(1) wrapping the blood pressure cuff around an upper limb of a given subject; inflating the blood pressure cuff until the blood pressure cuff pressure exceeds the systolic blood pressure of the given subject; and then deflating the blood pressure cuff slowly to obtain a mean blood pressure value BP0 of the given subject, recording the mean blood pressure value BP0 in a memory of the microprocessor;

(2) inflating the blood pressure cuff until the blood pressure cuff pressure exceeds the systolic blood pressure of the given subject, and then deflating the blood pressure cuff slowly to obtain a series of discrete cuff pressure values P and a series of discrete corresponding Korotkoff's sound delay times Tk, when the mean blood pressure value of the given subject is BP0, recording the series of discrete cuff pressure values P and the series of discrete corresponding Korotkoff's sound delay times Tk in the memory of the microprocessor, wherein the Korotkoff's sound delay time is defined as a time interval between a fixed time reference point and an arrival time of a corresponding Korotkoff's sound, the fixed time reference point is an ECG R wave peak or an ascending edge of a pulse wave, wherein the Korotkoff's sound sensor sends arrival time data of Korotkoff's sound to the microprocessor through the signal processing circuit and the ECG electrode sends heart beating data to the microprocessor through the signal processing circuit, and the microprocessor thus runs data analyzing software to calculate the Korotkoff's sound delay time and save the Korotkoff's sound delay time in the memory of the microprocessor;

(3) using the microprocessor running computing software to quadratic curve fit the series of discrete cuff pressure values P and the series of discrete corresponding Korotkoff's sound delay times Tk obtained in step (2) and thus obtaining a curve line representing a relationship between the cuff pressure value P and the corresponding Korotkoff's sound delay times Tk, and then using the microprocessor running computing software to construct a function Tk=H(P) describing the relationship between the Korotkoff's sound delay time Tk and the cuff pressure P based on the curve line, wherein Tk=H(P)=$k_1P^2+k_2P+k_3$, wherein k1, k2 and k3 are coefficients of the function and are obtained after the quadratic curve fitting;

(4) using the microprocessor running computing software to construct a function $$g(P) = \frac{dT_K}{dP} = 2k_1P + k_2$$

by differentiating the function Tk=H(P)=$k_1P^2+k_2P+k_3$ obtained from the step (3), the function $$g(P) = \frac{dT_K}{dP} = 2k_1P + k_2$$

representing the change in Korotkoff's sound delay time per unit change in cuff pressure;

(5) measuring an actual blood pressure of the given subject when the given subject makes moves that change its blood pressure, the moves including deep breathing or body posture changes, the measuring including:
wrapping the blood pressure cuff around the upper limb of the give subject,
setting a cuff pressure Pm at a value between the systolic blood pressure and the diastolic blood pressure of the given subject, and obtaining a Korotkoff's sound delay time Tkm corresponding to the cuff pressure Pm;

(6) using the microprocessor running computing software to calculate a Korotkoff's sound delay time Tkm0 by applying the value of the cuff pressure Pm to the function Tk=H(P)=$k_1P^2+k_2P+k_3$ obtained from step (3), the Korotkoff's sound delay time Tkm0 and the Korotkoff's sound delay time Tkm being different since the given subject makes moves that change its blood pressure;
calculating ΔTkm=Tkm−Tkm0, and recording a value of ΔTkm in the memory of the microprocessor;
calculating g(Pm) by substituting with the value of the cuff pressure Pm in the function $$g(P) = \frac{dT_K}{dP} = 2k_1P + k_2$$

obtained from step (4), because g(Pm) also equals to ΔTkm/ΔBPm according to a definition that g(P) also represents the change in Korotkoff's sound delay time per unit change in blood pressure when the pressure of the blood pressure cuff is stable, in which ΔBPm=BP−BP0, which is the difference between the actual blood pressure corresponding to the Korotkoff's sound delay time Tkm and the mean blood pressure BP0 obtained from step (1), and thus calculating ΔBPm based on the function ΔBPm=ΔTkm/g(Pm); and (7) using the microprocessor running computing software to obtain the actual blood pressure BP of the given subject by adding BP0 and ΔBPm, wherein BP=BP0+ΔBPm.

2. A method of measuring beat-to-beat arterial blood pressure, by using instruments including a blood pressure cuff, an inflating unit and a deflating unit for the blood pressure cuff, a cuff pressure sensor, a Korotkoff's sound sensor, an ECG electrode, a microprocessor, a signal processing circuit connected between the cuff pressure sensor, the Korotkoff's sound sensor and the microprocessor, and an ECG circuit connected between the ECG electrode and the microprocessor, comprising the steps of:

(1) wrapping the blood pressure cuff around an upper limb of a given subject; inflating the blood pressure cuff until the blood pressure cuff pressure exceeds the systolic blood pressure of the given subject; and deflating the blood pressure cuff slowly to obtain a mean blood pressure value BP0 of the given subject, recording the mean blood pressure value BP0 in a memory of the microprocessor;

(2) inflating the blood pressure cuff until the blood pressure cuff pressure exceeds the systolic blood pressure of the given subject, and then deflating the blood pressure cuff slowly to obtain a series discrete data of cuff pressure value P and a series of discrete data of corresponding Korotkoff's sound delay times Tk, when the mean blood pressure value of the given subject is BP0, recording the series of discrete data of cuff pressure values P and the series of discrete data of corresponding Korotkoff's sound delay times Tk in the memory of the microprocessor, wherein the Korotkoff's sound delay time is defined as a time interval between a fixed time reference point and an arrival time of a corresponding Korotkoff's sound, the fixed time reference point is an ECG R wave peak or an ascending edge of a pulse wave, wherein the Korotkoff's sound sensor sends arrival time data of Korotkoff's sound to the microprocessor through the signal processing circuit and the ECG electrode sends heart beating data to the microprocessor through the signal processing circuit, and the microprocessor thus runs data analyzing software to calculate the Korotkoff's sound delay time and save the the Korotkoff's sound delay time in the memory of the microprocessor;

(3) using the microprocessor to running computing software to quadratic curve fitt the series of discrete data of cuff pressure values P and the series of discrete data of corresponding Korotkoff's sound delay times Tk obtained in step (2) and thus obtaining a curve line representing a relationship between the cuff pressure value P and the corresponding Korotkoff's sound delay times Tk, and then using the microprocessor running computing software to construct a function Tk=H(P) describing the relationship between the Korotkoff's sound delay time Tk and the cuff pressure P based on the obtained curve line, wherein Tk=H(P)=$k_1P^2+k_2P+k_3$, wherein k1, k2 and k3 are coefficients of the function and are obtained after the quadratic curve fitting;

(4) using the microprocessor running computing software to construct a function $$g(P) = \frac{dT_K}{dP} = 2k_1P + k_2$$

by differentiating the function Tk=H(P)=$k_1P^2+k_2P+k_3$ obtained from the step (3); the function $$g(P) = \frac{dT_K}{dP} = 2k_1P + k_2$$

represents the change in Korotkoff's sound delay time per unit change in cuff pressure;

(5) when measuring a beat-to-beat blood pressure of the given subject, setting a pressure of the blood pressure cuff at the mean value BP0 between the systolic blood pressure and the diastolic blood pressure of the given subject, obtaining a series of Korotkoff's sound delay times T(i) for each heart beat and recording the series of Korotkoff's sound delay times T(i) in the memory of the microprocessor;

(6) using the microprocessor running computing software to differentiate T(i) and obtaining a series of T'(i), wherein T'(i)=T(i+1)−T(i) represents Korotkoff's sound delay time change between each heart beat and a preceding heart beat, and wherein i=1, 2, 3 . . .

(7) using the microprocessor running computing software to calculate the blood pressure change between each beat by using the function $\Delta BP(i)=T'(i)/g(P_i)$, which is based on the definition that g(P) also representing the change in Korotkoff's sound delay time per unit change in blood pressure when setting the pressure of the blood pressure cuff at the mean value between the systolic blood pressure and the diastolic blood pressure of the given subject, and wherein $g(P_i)$ is obtained from the function $$g(P) = \frac{dT_K}{dP} = 2k_1P + k_2$$

obtained from the step (4), and T'(i) is obtained from the step (6), wherein Pi is a cuff pressure value corresponding to the T'(i); and (8) using the microprocessor running computing software to calculate a beat-to-beat blood pressure change BP(n) by using the function $$BP(n) = \sum_{i=1}^{n} \Delta BP(i);$$

wherein n=1 . . . m−1, m is the number of heartbeat cycles, and ΔBP(i) is obtained from the step (7).

* * * * *